United States Patent [19]
Welch et al.

[11] Patent Number: 5,986,120
[45] Date of Patent: Nov. 16, 1999

[54] METAL TRIFLIMIDE COMPLEXES

[75] Inventors: John T. Welch; Rolf Claessen; Silvana Ngo, all of Albany, N.Y.

[73] Assignee: The Research Foundation of the State University of New York, Albany, N.Y.

[21] Appl. No.: 09/021,253

[22] Filed: Feb. 10, 1998

[51] Int. Cl.[6] .............................. C07F 17/00; C07F 7/28; C08F 4/64

[52] U.S. Cl. ......................... 556/53; 526/160; 526/189; 526/346; 526/943; 502/155; 502/168

[58] Field of Search ............................... 556/53; 526/160, 526/189, 346, 943; 502/155, 168

[56] References Cited

FOREIGN PATENT DOCUMENTS

| | | |
|---|---|---|
| 09 57 110 | 3/1997 | Japan . |
| 09 169 690 | 6/1997 | Japan . |
| 09 176 063 | 7/1997 | Japan . |
| 4092411315 | 9/1997 | Japan . |

OTHER PUBLICATIONS

Mikami et al., "Metal Bis(trifluormenthylsulfonyl)amides as Highly Efficient Lewis Acid Catalysts for Acylation Reactions, "SYNLETT, Feb. 1996, pp. 171–172.

Siedle et al., "Reactions of Bis(cyclopentadienyl)Dimethyizirconium With Fluorocarbon Acids. Structure, Dynamic Properties, and $^{91}$Zr NMR Spectra of $(C_5H_5)_2$Zr $[HC(SO_2CF_3)_2-0,0']$ $[HC(SO_2CF_3)_2-0]$," Organometallics, vol. 9, No. 4, 1990, pp.1290–1295.

*Primary Examiner*—Porfirio Nazario-Gonzalez
*Attorney, Agent, or Firm*—Heslin & Rothenberg, P.C.

[57] ABSTRACT

A composition relating to metal-triflamide complexes useful as catalysts for the syndiotactic polymerization of styrene is disclosed.

10 Claims, No Drawings

METAL TRIFLIMIDE COMPLEXES

STATEMENT AS TO THE RIGHTS UNDER FEDERALLY SPONSORED RESEARCH

This invention may have been made with support from the National Science Foundation (Grant No. NSF CHE 9413004). The United States government may have certain rights in the invention.

FIELD OF THE INVENTION

The invention relates to metal triflimide complexes for the syndiotactic polymerization of styrene.

BACKGROUND OF THE INVENTION

Syndiotactic polystyrenie is a commercially important material useful in the preparation of articles and objects having an extremely high resistance to deformation due to the effects of temperature. The polymers have very high melting points and low solubility in organic solvents, due to a stereoregular structure, composed of phenyl groups alternating regularly from side to side of the chain.

Transition metal complexes have been used as Ziegler-Natta catalysts for the polymerization of olefins, including stereo specific polymerizations. For example, Group 4 half-sandwich complexes, such as titanocene, zirconocene or hafnocene derivatives, activated with methyl aluminoxane (MAO) are efficient homogeneous catalysts for the promotion of syndioselective polymerization of styrene. More recently, metal complexes of composition $CpML_2+A^-$, where Cp is substituted or unsubstituted cyclopentadienyl, M is a transition metal, L is an anionic ligand, and A is a noncoordinating, compatible anion of a Bronsted acid salt, for example tetraphenyl borate, are have been used for syndiotactic polymerization of styrene. Formation of these metal-borate complexes requires an additional step in the polymerization process, however, and therefore increases production costs. A need exists for methylaluminoxane cocatalysts which do not require the preformation of the metal-borate complex, and which produce syndiotactic polystyrene in high yield.

SUMMARY OF THE INVENTION

It is therefore an object of this invention to provide materials which can be cocatalysts with methylaluminoxane, without additional components, for the syndiotactic polymerization of styrene. It is a further object to provide for a two-step synthesis of the cocatalyst from commercially available starting materials, in high yield, without the need for purification of the product.

In one aspect, the invention relates to a composition of formula $R^1M(R^2)_n(N(SO_2CF_3)_2)_{3-n}$, wherein M is Ti, or Zr; $R^1$ is indenyl, cyclopentadienyl or pentamethylcyclopentadienyl, $R^2$ is independently indenyl, cyclopentadienyl, pentamethylcyclopentadienyl, methyl, methoxy, hydroxy, 2,4,6-trimethylphenoxy, trifluoroethoxy, hexafluoroisopropoxy, or chloro, and n=1 or 2. Preferably, n=1 and M=Ti. More preferably, $R^2$=cyclopentadienyl or methoxy, n=1 and M=Ti.

In another aspect, the invention relates to a process for the production of the metal triflimides described above, comprising reacting $AgN(SO_2CF_3)_2$ with $R^1R^2MCl_2$ in a suitable solvent, and removing the solvent.

In yet another aspect, the invention relates to a process for the production of highly syndiotactic polystyrene, comprising premixing the composition described above with methylaluminoxane and combining the catalyst premix with styrene, at a temperature of 25–100° C. Preferably, the molar ratios of styrene, methlylaluminoxane and metal triflimide complex are 6000/400–600/0.5–2. The process may additionally comprise a solvent.

DETAILED DESCRIPTION OF THE INVENTION

"Syndiotactic" as used herein refers to polystyrene having a stereoregular structure of greater than 80% as determined by extraction with methyl ethyl ketone (MEK). The weight of syndiotactic polystyrene is obtained from the MEK-insoluble portion and that of atactic polystyrene from the soluble fraction. The polymer tacticity may be confirmed by IR spectroscopy.

The compositions of the invention are described by the formula $R^1M(R^2)_n(NTf_2)_{3-n}$, wherein M is Ti, or Zr; Tf is $SO_2CF_3$, $R^1$ is indenyl, cyclopentadienyl (Cp) or pentamethyl cyclopentadienyl (Cp*), $R^2$ is independently indenyl, cyclopentadienyl, pentamethylcyclopentadienyl, methyl, methoxy, hydroxy, 2,4,6-trimethylphenoxy, trifluoroethoxy, hexafluoroisopropoxy, or chloro, and n=1 or 2. Preferred substituents for $R^2$ are cyclopentadienyl and methoxy. A preferred metal M is titanium.

The triflimide complexes of the invention may be prepared by the reaction of one or two equivalents of $AgNTf_2$ with complexes $R^1R^2MCl_2$, where $R^1$ and $R^2$ are as defined above. For $R^1$, $R^2$=Cp, M=Ti, and n=1 starting material $Cp_2TiCl_2$ is commercially available from Aldrich Chemical Co. For $R^1$=Cp and M=Ti, starting material $CpTiCl_3$ is commercially available. For $R^1$=Cp*, the starting material $Cp*MCl_3$ can be prepared according to the procedure of Threlkel, et al., *J. Organometal, Chem.*, 1977, 1. The $Cp*MR^2Cl_2$ complexes are prepared by the reaction of an excess of the corresponding $R^2H$ compound with $Cp*MCl_3$. The zirconium and silver metal complexes may also be prepared by these same reactions.

Reaction of the dichloride complexes with one equivalent of $AgNTf_2$ gives the mono-triflimide complexes of the invention; with two equivalents of $AgNTf_2$, the bis-triflimides are produced. $AgNTf_2$ is prepared from the lithium salt $LiNTf_2$ obtained from the 3M corporation through the imide. The reaction may be conducted at temperatures of 0–50° C., preferably at about 25° C., for a time sufficient to fully react the starting materials. Typical reaction times are about two hours. Light should be excluded from the reaction. The product may be isolated by removal of the solvent under vacuum, extraction of the residue into toluene and evaporation of the toluene under vacuum. The hydroxy complex may be prepared by the reaction of the corresponding triflimide complex, where $R^2$ is methyl, with one equivalent of water in diethyl ether.

The metal triflimide complexes of the invention may be used as cocatalysts with methylaluminoxane for the syndiotactic polymerization of styrene. Methylaluminoxane (hereinafter MAO) may be prepared according to any known technique, including, for example, the reaction of trimethylalluminum and a hydrated metal salt as taught by U.S. Pat. No. 4,544,762, and is commercially available. For purposes of calculating the molar ratio of MAO to metal triflimide cocatalyst, MAO is assigned a repeating unit structure corresponding to the formula —Al(CH$_3$)O— with a unit molecular weight of 100.03.

The triflimides arc normally combined with MAO in the presence of an aliphatic, cycloaliphatic or aromatic solvent or a combination of such solvents. The components are employed in quantities which provide an atomic ratio of Al:M suitably from about 10:1 to about 50,000:1, more suitably from about 50:1 to about 10,00:1, most suitably from about 100:1 to about 1000:1.

The cocatalysts may be combined in any order in an inert atmosphere such as nitrogen, argon, xenon, or combinations thereof. The components are mixed at any suitable temperature, preferably from about 0° C. to about 50° C., more suitably about 25° C.

The polymerization is conducted at temperatures of from about 25° C. to about 100° C., preferably from about 30° C. to about 60° C. for a time sufficient to produce the desired polymer. Typical reaction times are from several minutes to several hours, commonly from about one to ten hours. The optimum time will vary depending on the temperature, solvent, and other reaction conditions employed.

The polymerization can be conducted at subatmospheric pressure as well as superatmospheric pressure. It is preferred that near atmospheric pressure be employed.

The polymerization is normally conducted in the presence of an inert solvent as a diluent. Examples include aliphatic, cycloaliphatic, aromatic, and halogenated aromatic hydrocarbons, as well as mixtures thereof. Preferred solvents are linear and branched $C_4$ to $C_{20}$ alkanes, toluene, and mixtures thereof. Suitable amounts of solvent are employed to provide a monomer concentration from about 5% to about 100% by weight.

Purification of the resulting polymer to remove entrained catalyst may be desired. The presence of entrained catalyst may be determined from ash residues from pyrolysis of the polymer that are attributable to aluminum and titanium values. A suitable technique for removing such compounds is solvent extraction utilizing hot, high boiling chlorinated solvents, followed by filtration.

EXAMPLES

Example 1

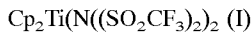

$Cp_2Ti(N((SO_2CF_3)_2)_2$ (I)

$AgN(SO_2CF_3)_2$. The imide $HN(SO_2CF_3)$, was obtained from the lithium salt. $LiN(SO_2CF_3)_2$ (10 g, 35 mmole) was added to 50 mL concentrated sulfuric acid. The free imide was distilled at about 90° C., 10 mm Hg and purified by sublimation at about 70° C., 1–2 mm Hg giving 7.4 g (74%) $HN(SO_2CF_3)_2$. The silver salt was then obtained from the imide. $Ag_2CO_3$ (2.0 g, 0.2 mmol) was added slowly to a stirring, solution of $HN(SO_2CF_3)_2$ (3.5 g, 12.0 mmole) in 25 mL water. The mixture was then digested, wrapped in foil, at 60° C. for 1 h and the excess $Ag_2CO_3$ filtered off. The water was removed under vacuum giving white powder of $AgNTf_2$. Dissolution of the powder in diethyl ether (25 mL) followed by filtration and removal of all volatiles under vacuum gave 4.6 g (95%) of white $AgNTf_2$.

A solution of $AgNTf_2$ (0.140 g, 0.361 mmole) in 5 mL diethyl ether was added to a stirring slurry of $Cp_2TiCl_2$ (0.045 g, 0.18 mmole) in 7 mL diethyl ether. After stirring at room temperature for 3 h (wrapped in foil), the mixture was filtered and all volatiles removed in vacuo giving a yellow brown oil. The oil was washed with pentane and extracted with toluene (5 mL). Removal of the solvent under vacuum gave 0.076 g (57%) of I as an orange residue.

Example 2

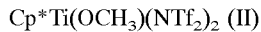

$Cp*Ti(OCH_3)(NTf_2)_2$ (II)

$Cp*Ti(OCH_3)Cl_2$. $Cp*TiCl_3$ (0.200 g, 0.691 mmol) was weighed into a 50 ml Schlenk flask and 2.0 ml methanol was added. The solution was refluxed for one hour, then cooled to room temperature and then in an ice bath. Orange crystals slowly formed. The mother liquor was syringed out, and the crystals were dried under vacuum.

A solution of $AgNTf_2$ (0.123 g, 0.316 mmole) in 5 mL, diethyl ether was added to a stirring solution of $Cp*TiCl_2$ ($OCH_3$) (0.045 g, 0.16 mmole) in 5 mL diethyl ether. After stirring at room temperature for 2 h (wrapped in foil), the mixture was filtered and all volatiles removed in vacuo giving a red orange oil. The oil was washed with pentane and extracted with toluene (5 mL). Removal of the toluene under vacuum gave 0.110 g (90%) II as red orange residue.

Example 3

Syndiotactic Polymerizations of Styrene with MAO

A styrene:Al: catalyst ratio of 6000:500:1 was effected after U.S. Pat. No. 5,045,517. Into one 100 mL Schlenk flask were added 0.05 g (0.07 mmol) $Cp_2Ti(NTf_2)_2$ catalyst and 5 mL toluene, and into another, 4.2 mL of a 10% solution (3.7 mmol) of MAO in toluene and toluene (5 mL). The mixtures were combined, stirred for 15 minutes at room temperature and then transferred to an oil bath at 50° C. Styrene (5.0 mL, 44 mmoles) was added. The mixture was allowed to stir for 3 hours and was quenched by the addition of 20 mL of methanol. The mixture was poured into 50 mL of 3% HCl in methanol, was diluted with additional methanol to the 200 mL mark and was stirred for 1 hour. The precipitated polystyrene (PS) was separated by filtration and was weighed after drying in a 100° C. vacuum oven for 24 hours. Both the insoluble portion and the soluble fraction (reprecipitated from methanol) were again dried at 100° C. in vacuo for 24 hours. The weight of syndiotactic polystyrene (SPS) was obtained from the 2-butanone-insoluble portion and that of atactic polystyrene (APS) from the soluble fraction. The polymer obtained was 93% syndiotactic polystyrene. The polymer tacticity was confirmed by IR spectroscopy.

We claim:

1. A composition of formula $R^1M(R^2)_n(N(SO_2CF_3)_2)_{3-n}$, wherein M is Ti; $R^1$ is indenyl, cyclopentadienyl or pentamethylcyclopentadienyl, $R^2$ is indenyl, cyclopentadienyl, pentamethylcyclopentadienyl, methyl, methoxy, hydroxy, or 2,4,6-trimethylphenoxy, trifluoroethoxy, hexafluoroisopropoxy, or chloro, and n=1 or 2.

2. The composition of claim 1, wherein n=2.

3. The composition of claim 1, wherein $R^2$ is cyclopentadienyl or methoxy.

4. The composition of claim 1, wherein $R^2$ is cyclopentadienyl or methoxy, and n=2.

5. A process for the production of a composition of formula $R^1M(R^2)_n(N(SO_2CF_3)_2)_{3-n}$, wherein M is Ti, or Zr; $R^1$ is indenyl, cyclopentadienyl or pentamethylcyclopentadienyl, $R^2$ is indenyl, cyclopentadienyl, pentamethylcyclopentadienyl, methyl, methoxy, hydroxy, or 2,4,6-trimethylphenoxy, trifluoroethoxy, hexafluoroisopropoxy, or chloro, and n=1 or 2, comprising reacting $AgN(SO_2CF_3)_2$ with $R^1R^2MCl_2$ in a suitable solvent, and removing said solvent.

6. A process for the production of syndiotactic polystyrene, comprising premixing, a catalyst composition according to claim 1 with methylaluminoxane and combining said premix with styrene, at a temperature of 25–100° C.

7. The process of claim 6, wherein molar ratios of styrene, methylaluminoxane and catalyst are 6000/400–600/0.5–2.

8. The process of claim 6, additionally comprising combining a solvent with said premix.

9. A composition of formula $R^1M(R^2)_n(N(SO_2CF_3)_2)_{3-n}$, wherein M is Zr; $R^1$ is indenyl, cyclopentadienyl or pentamethylcyclopentadienyl, $R^2$ is indenyl, pentamethylcyclopentadienyl, methyl, methoxy, hydroxy, or 2,4,6-trimethylphenoxy, trifluoroethoxy, hexafluoroisopropoxy, or chloro, and n=1 or 2.

10. A process for the production of syndiotactic polystyrene, comprising premixing a catalyst composition according to claim 9 with methylaluminoxane and combining said premix with styrene, at a temperature of 25–100° C.

* * * * *

UNITED STATES PATENT AND TRADEMARK OFFICE
CERTIFICATE OF CORRECTION

PATENT NO. : 5,986,120
DATED : November 16, 1999
INVENTOR(S) : Welch et al.

It is certified that error appears in the above-identified patent and that said Letters Patent is hereby corrected as shown below:

IN THE CLAIMS:

Claim 2, Col. 4, line 46, delete "n=2" and replace with --n=1--.

Claim 4, Col. 4, line 50, delete "n=2" and replace with --n=1--.

Signed and Sealed this

Twenty-first Day of November, 2000

*Attest:*

Q. TODD DICKINSON

*Attesting Officer*   *Director of Patents and Trademarks*